United States Patent [19]
Brass et al.

[11] Patent Number: 5,804,822
[45] Date of Patent: Sep. 8, 1998

[54] FAULT LOCATING DEVICE, SYSTEM AND METHOD

[75] Inventors: Jack Brass, North York; Steven Goldfarb, Willowdale, both of Canada

[73] Assignee: Brasscorp. Ltd., Toronto, Canada

[21] Appl. No.: 755,851

[22] Filed: Dec. 9, 1996

Related U.S. Application Data

[63] Continuation of Ser. No. 417,234, Apr. 5, 1995, abandoned.

[51] Int. Cl.⁶ .................................................. G01N 21/64
[52] U.S. Cl. ........................................ 250/302; 250/461.1
[58] Field of Search ................................ 250/302, 461.1, 250/504 H

[56] References Cited

U.S. PATENT DOCUMENTS

| | | | |
|---|---|---|---|
| 2,525,914 | 10/1950 | Knauth | 73/229 |
| 3,136,890 | 6/1964 | Wain | 250/504 H |
| 3,590,256 | 6/1971 | Neeff | 250/218 |
| 3,666,945 | 5/1972 | Frungel et al. | 250/461.1 |
| 3,736,428 | 5/1973 | Monroe | 250/461.1 |
| 3,875,094 | 4/1975 | Schroeter et al. | 260/28 |
| 3,925,666 | 12/1975 | Allan et al. | 250/338 |
| 4,270,049 | 5/1981 | Tanaka et al. | 250/227 |
| 4,298,806 | 11/1981 | Herold | 250/504 H |
| 4,336,459 | 6/1982 | Fay | 250/461.1 |
| 4,365,153 | 12/1982 | Seigel et al. | 250/253 |
| 4,487,075 | 12/1984 | Karidis | 73/861.05 |
| 4,689,484 | 8/1987 | McMahon | 250/227 |
| 5,191,261 | 3/1993 | Mass | 315/171 |
| 5,200,801 | 4/1993 | Juvinall et al. | 356/428 |
| 5,265,640 | 11/1993 | St. Amant | 137/114 |

FOREIGN PATENT DOCUMENTS

| | | |
|---|---|---|
| 2200364 | 3/1997 | Canada . |
| 2200365 | 3/1997 | Canada . |

OTHER PUBLICATIONS

"Short Arc Lamps: A User's Guide", from the Photonics Design And Applications Handbook, 1990.

"Optimization of magnetic powder testing with ultraviolet light", Obering.N. Riess, Hamburg, 2034 Schweissen & Schneiden 45 (1993)Juni, No. 6, Dusseldorf, DE.

*Primary Examiner*—Jack I. Berman
*Attorney, Agent, or Firm*—Fitzpatrick, Cella, Harper & Scinto

[57] ABSTRACT

A lamp system is for use in non-destructive testing to illuminate luminescent materials, such as fluorescent dyes. The lamp system has a control unit and a lamp. The lamp has a bulb and a filter. The bulb generates at least a first wavelength of invisible energy and the filter limits other visible wavelength light from the lamp. The lamp has a handle with a trigger. The control unit pulses the lamp on and off when the trigger is depressed. The luminescent material absorbs the first wavelength of energy and pulses in response when the lamp illuminates the material. The system can be AC or DC operated. It can be operated from an automotive battery.

27 Claims, 5 Drawing Sheets

FAULT LOCATING DEVICE, SYSTEM AND METHOD

This application is a continuation of application Ser. No. 08/417,234, filed Apr. 5, 1995, now abandoned.

FIELD OF THE INVENTION

The invention relates to devices for locating faults in machinery and equipment. More particularly, it relates to devices and methods of using lamps and dyes for locating such faults.

BACKGROUND OF THE INVENTION

Luminescent materials are often used to detect faults, such as leaks. For example, a fluorescent dye is injected or poured into a system. Where a leak occurs the dye will escape from the system. Shining a light of appropriate wavelength (typically ultraviolet) on the system will cause the dye to fluoresce. The existence and location of a leak or leaks are then evident. When performed in total darkness the outcome of such a procedure is often enhanced; however, total darkness is often not available in testing environments, such as an outdoor air conditioner where the sun cannot be shut off, or a shop floor where darkness may be dangerous when machinery in motion is involved.

Unfortunately, visible (including ambient) light competes with the fluorescence from dye for the attention of the person conducting the test. This is particularly true where the system has shiny surfaces that reflect visible or ambient light.

Similarly, luminescent materials are also used in non-destructive testing. For example, fluorescent dyes combined with iron filings can be used to detect faults such as stress fractures. The combination of iron filings and fluorescent dye is attracted to the faults and, again, the dye emits visible light when illuminated by appropriate incident wavelength light. Even though non-destructive testing may be stringently regulated, the emitted light from a very small fault is often difficult to detect even though a very small fault may present a potentially great danger. Any assistance in identifying these faults would be helpful.

Other concerns with existing ultraviolet lamps are their cost, size and power consumption. For low power consumption and cost, fluorescent lamps can be used to generate the incident radiation. However, fluorescent lamps generate a low intensity of incident ultraviolet radiation. It is desirable to be able to bring the lamp in to close proximity with the fault. This is often difficult in the tight spaces available when working around machinery and equipment.

It is an object of the invention to address these or other problems associated with the use of lamps in the location of faults in machinery and equipment.

SUMMARY OF THE INVENTION

In a first aspect the invention provides a lamp system for locating faults using luminescent material that absorbs electromagnetic radiation of a first wavelength, converts that energy and emits a second visible wavelength light. The system has a lamp for generating incident electromagnetic radiation of the first wavelength and otherwise limited amounts of visible light. It also has a control unit for pulsing the incident radiation lamp on and off. The material on which the lamp is shone will emit radiation of the second wavelength pulsing on and off.

The control unit may repeatedly pulse the incident radiation on and off. The lamp may have a bulb and a filter. The bulb is for emitting electromagnetic radiation of at least the first wavelength. The filter is for allowing electromagnetic energy of the first wavelength to emit from the lamp, while the filter limits visible light outside of the first wavelength from emitting from the lamp.

The control unit may be further for powering the lamp at a higher voltage than nominal rating for the lamp. The first wavelength may be invisible to an unaided eye. The first wavelength may be approximately 360 nanometers. The lamp may pulse at a frequency between 0.5 and 3 Hz.

The lamp may have a handle for an operator to hold and aim the lamp, and a switch adjacent the handle for one handed operation of the lamp.

Where there is a bulb it may be a halogen bulb. Alternatively, the bulb may be a mercury vapour bulb. With the mercury vapour bulb, the control unit may have a strobing circuit for pulsing the bulb on and off and the control unit may have a ballast.

As a further alternative, the bulb may be an elongated fluorescent tube. The lamp may have an elongate back casing for receiving the tube, the back casing open on one side and coated internally with a reflective material. A shield may enclose the back casing over the tube. The shield is transmissive of the first wavelength radiation. The back casing and the shield may extend into a housing for the control unit which is at least partially formed on a printed circuit board extending from the shield into the housing. The casing may have a U-shaped profile and opposing slots into which the shield is placed.

In a second aspect the invention provides a lamp system for locating faults using luminescent material that absorbs electromagnetic radiation of a first ultraviolet wavelength, converts that energy and emits a second visible wavelength light. In this aspect the lamp system has a lamp for generating incident electromagnetic radiation of the first ultraviolet wavelength. The lamp is also for limiting the emission of visible light. The lamp system also has a control unit for pulsing the lamp on and off. Luminescent material on which the lamp is shone will emit radiation of the second wavelength pulsing on and off.

In a third aspect the invention provides a lamp system for locating faults using luminescent material that absorbs electromagnetic radiation of a first wavelength, converts that energy and emits a second visible wavelength light. The system has a lamp for generating incident electromagnetic radiation of the first wavelength and otherwise limited amounts of visible light. The system also has a control unit for pulsing the lamp on and for pulsing the lamp off.

There is a duration between the lamp pulsing off and the lamp pulsing on, the duration is greater than the time it takes for the material to cease emitting radiation after the lamp is pulsed off. The material on which the lamp is shone will emit radiation of the second wavelength pulsing on and off.

The material may be fluorescent. Alternatively, it may be phosphorescent.

In a fourth aspect the invention provides a kit with a lamp system having a lamp for generating incident electromagnetic radiation of the first wavelength and otherwise limited amounts of visible light. The lamp system also has a control unit for pulsing the lamp on and off. The kit also has a luminescent material that absorbs electromagnetic radiation of a first wavelength, converts that energy and emits a second visible wavelength light. Luminescent material on which the lamp is shone will emit radiation of the second wavelength pulsing on and off.

In a fifth aspect the invention provides a method of locating luminescent material that absorbs electromagnetic energy of a first wavelength, converts that energy and emits a second substantially different visible wavelength. The method employs at least two steps. It generates from a lamp incident electromagnetic energy of the first wavelength and otherwise limited amounts of visible light. It pulses the lamp on and off. As a result, the luminescent material fluoresces and pulses upon illumination by the lamp in accordance with pulses of energy emitted from the lamp.

The lamp may generate the incident electromagnetic energy at a higher than nominal voltage rating for the lamp. The incident light may be generated from a bulb in the lamp and the light may pass through a filter that allows the first wavelength light to pass and otherwise limits the amount of visible light.

In a sixth aspect the invention provides a lamp system for locating faults using luminescent material that absorbs electromagnetic radiation of a first wavelength, converts that energy and emits a second visible wavelength light. The system has a lamp for generating incident electromagnetic radiation of the first wavelength and otherwise limited amounts of visible light. It also has a control unit for pulsing the lamp on and off. The control unit is also for driving the lamp at a greater voltage than its nominal rating. Luminescent material on which the lamp is shone will emit radiation of the second wavelength pulsing on and off.

BRIEF DESCRIPTION OF THE DRAWINGS

For a better understanding of the present invention and to show more clearly how it may be carried into effect, reference will now be made, by way of example, to the accompanying drawing which shows the preferred embodiments of the present invention and in which.

DETAILED DESCRIPTION OF THE PREFERRED EMBODIMENT

Figure 1:
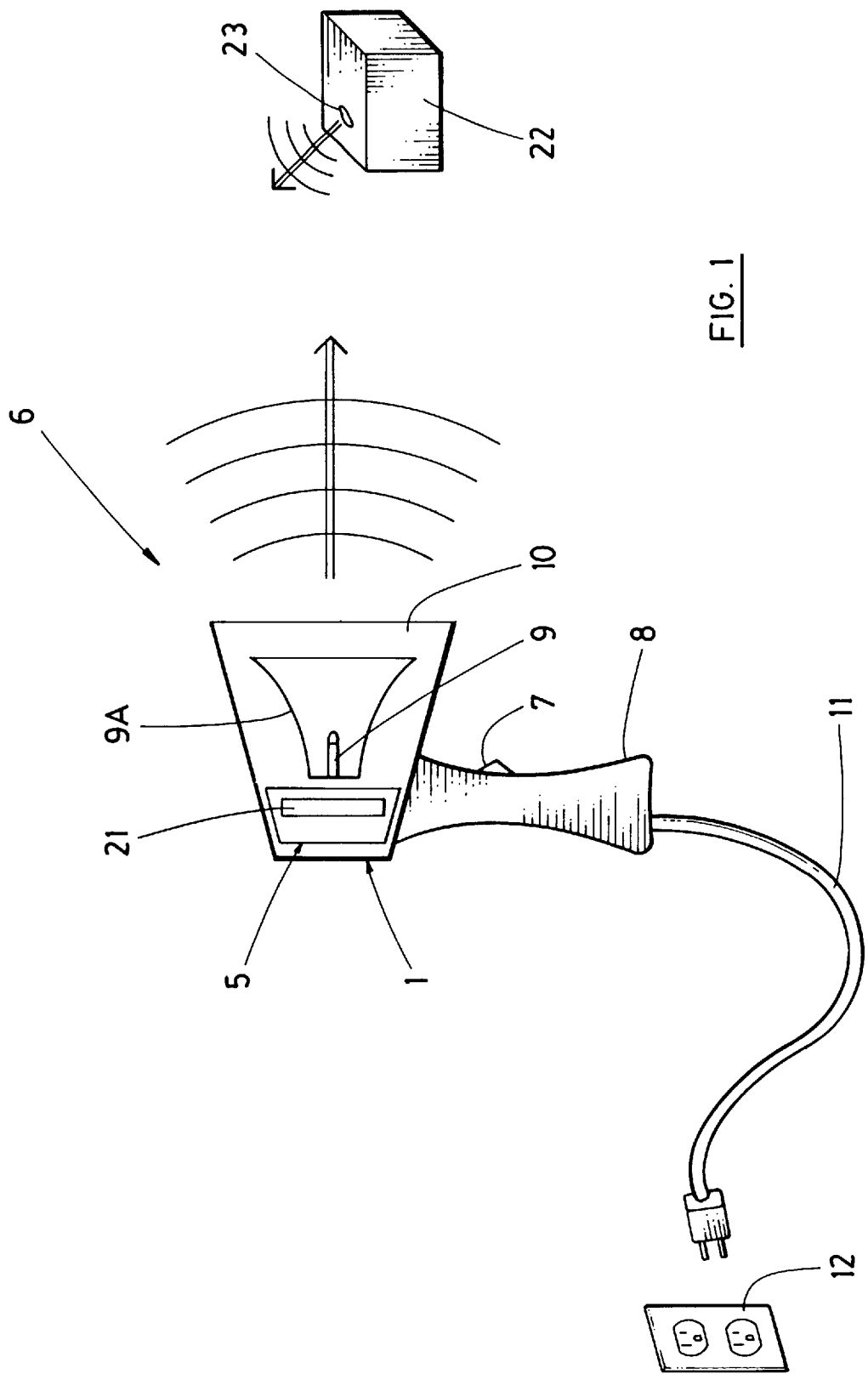
FIG. 1 is a diagrammatic side elevation view of a halogen lamp system according to a preferred embodiment of the invention when used in an automotive application.

Referring to FIG. 1, a lamp 1 contains a control unit 5. Together the lamp 1 and control unit 5 are a lamp system 6. The lamp 1 has a switch 7 on a handle 8. The lamp 1 also has a bulb 9 and reflector 9A. In this first preferred embodiment, the bulb 9 is a filament bulb 9, such as a tungsten halogen bulb 9. Halogen bulbs 9 give off a substantial amount of ultraviolet light without requiring a ballast. This allows the system 6 to be produced as a hand held model at a relatively inexpensive price.

Covering the bulb 9 is a filter 10. The filter 10, as is known in the art, allows the passage of incident light for the purpose of causing a chosen luminescent material to emit visible radiation at a substantially different wavelength than the incident light. The filter 10 limits the visible light incident from the lamp 1, other than that required to make the luminescent material emit the different wavelength visible radiation. As will be discussed further below, the filter 10 limits visible light as much as is practical given limitations on cost and available technology. As will also be discussed further below, it is possible that an embodiment of the lamp 1 could be made without the use of the filter 10 provided phosphorescent properties are exploited.

In this description the term "luminescent materials" is used to describe materials that are stimulated or excited by incident electromagnetic radiation of one wavelength, typically in the ultraviolet range, and return to their original state. As part of this process such materials emit visible light. In most cases the emitted radiation is of a substantially different wavelength from the incident radiation. The wavelengths are substantially different in the sense that an unaided eye can tell the difference between the different wavelengths. Certainly where the incident wavelength incident from the lamp 1 is invisible or barely visible ultraviolet light and the wavelength emitted from the luminescent material is visible light then the wavelengths will be substantially different.

In this description, luminescent materials include both fluorescent and phosphorescent materials. Fluorescent materials typically emit radiation within about 10 to the −8 power seconds after being stimulated, while phosphorescent materials emit after longer periods, up to hundreds of seconds. Luminescent materials are normally solids that are typically dissolved in solvents to create a solution for use in locating faults.

The lamp 1 has a cord 11 which may be plugged into an AC source 12. The switch 7 may be a momentary switch 7 turning on the lamp 1 only when the switch 7 is held by an operator. This prevents the lamp 1 from being left activated when not in use.

The control unit 5 can convert the source voltage to a given voltage for the bulb 9 that is greater than the nominal rating of the bulb 9. This can increase the intensity of ultraviolet exciting or stimulating incident radiation for the same bulb 9. The increase in intensity of ultraviolet radiation is often greater than the increase in the intensity of the visible wavelength radiation emitted from the bulb 9.

The control unit 5 has a strobing circuit 21 that pulses the power from the power source 12 when the switch 7 is on. The pulsed power from the control unit 5 is available to the bulb 9 when the switch 7 is depressed. The bulb 9 pulses on and off in accordance with the timing of the pulsed power from the control unit 5.

In operation, the control unit 5 is connected to the power source 12. An operator grips the handle 8 and aims the lamp 1 at an object that is being tested, for example an automotive air conditioning component 22. The switch 7 is depressed and the bulb 9 is pulsed on and off by the strobing circuit 21. Luminescent material 23 in solution that is leaking from a fault in the component 22 absorbs the incident light and emits visible radiation that pulses. The emitted pulsing radiation stands out to allow the operator to see it.

Even though some visible light (outside of the wavelength required to cause the luminescent material to emit) is allowed to pass through the filter 10 (see the discussion regarding FIG. 2 below), the enhanced visibility of the material 23 is not to be underestimated.

The quality of phosphorescence, a substantially delayed emission of visible radiation, can further enhance the visibility of the pulsing emitted radiation from the material 23 as undesired incident visible light from the lamp 1 is extinguished while emission from the material 23 occurs afterwards. The delay between the cessation of the incident radiation and the cessation of the emitted radiation does not have to be lengthy, only enough to increase the chance that the user will see the emitted radiation. Delays in the order of 30 milliseconds or more would likely be sufficient to take advantage of this property as the human eye typically takes 30 milliseconds to register any change. Longer delays would be advantageous. It is recommended to select the phosphorescent material so that the emitted radiation from the material ceases sufficiently prior to the next pulse of the lamp 1 in order to more easily distinguish one pulse from the next. When a phosphorescent material is used for the material 23, it is possible that the filter 10 could allow the transmission of incident light of a wavelength that is not substantially different from that of the emitted light as the incident light will have extinguished when the emitted light is continuing to emit.

Care must be taken in selecting appropriate luminescent materials, particularly phosphorescent materials, for specific applications. Many luminescent materials are quite abrasive and their use in specific applications could be contraindicated, for example when used as an additive to components with moving parts.

Figure 2:
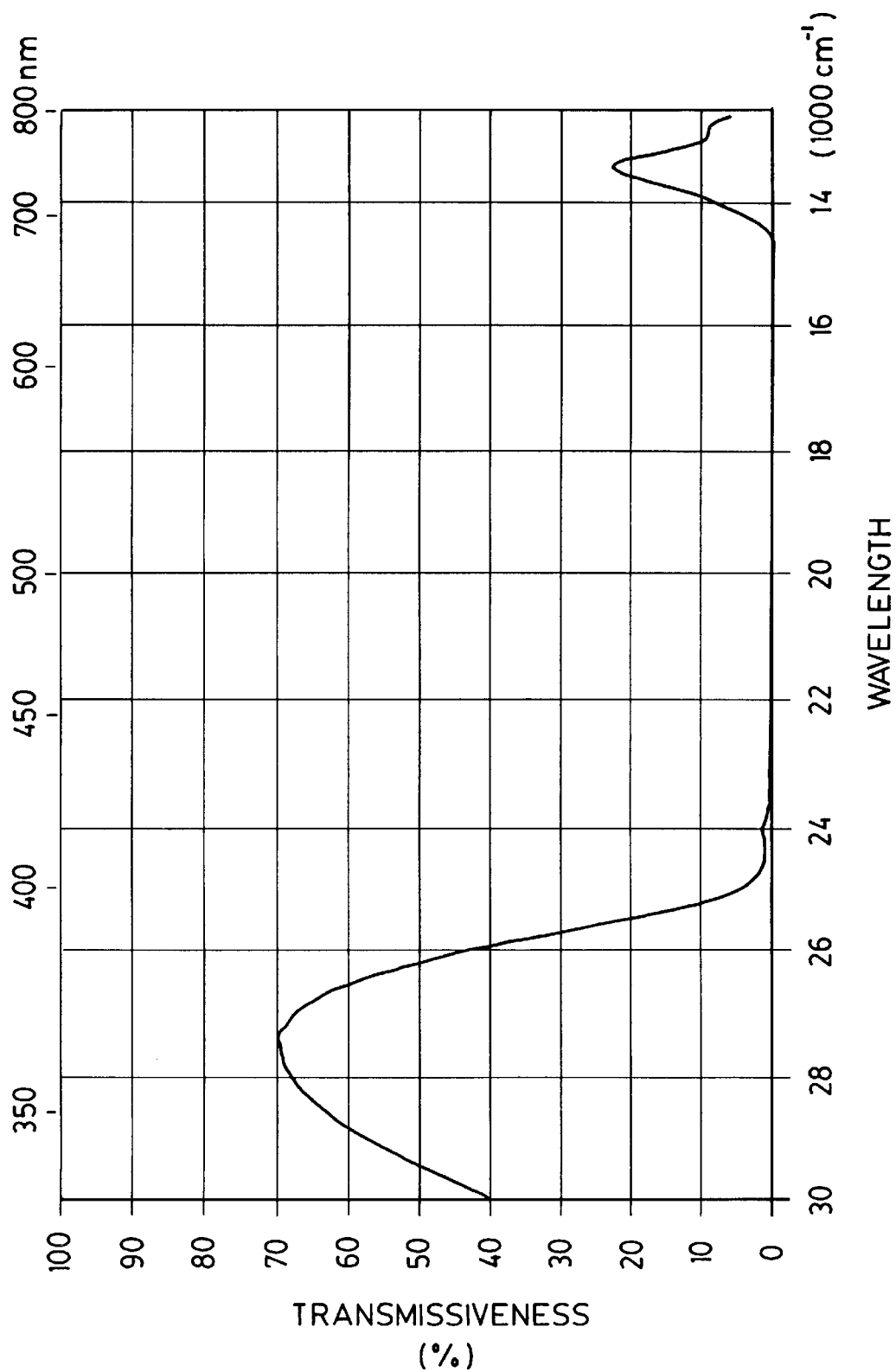
FIG. 2 is a graph of the light transmission characteristics of a filter employed in the lamp system of FIG. 1.

Referring to FIG. 2, as an example when the system 6 is to be used in conjunction with solvent yellow 43 fluorescent dye as the luminescent material, a Kopp™ No. 71 UV filter 10 allows appropriate wavelengths of light to pass peaked at approximately 360 nanometers wavelength light, while limiting the amount of visible light emitted from the lamp 1 to almost nil. Solvent yellow 43 emits yellow light of approximately 530 to 600 nanometers wavelength under incident ultraviolet light of a wavelength of approximately 360 nanometers. Solvent yellow 43 is fluorescent, but not phosphorescent.

In FIG. 2, the horizontal axis is the wavelength of light incident from the bulb 9, while the vertical axis is the percent transmissiveness of the filter 10 at a given wavelength.

The amount of filtering required for any particular application will depend on the relative amount of exciting or stimulating light generated from the bulb 9 versus the amount of visible light generated, particularly at or near enough to be confused with the wavelength of the emitted radiation from the luminescent material, The filter 10 is preferably selected to allow passage of the exciting or stimulating wavelength light while otherwise limiting visible light from the lamp 1.

The lamp 1 could also be used with luminescent materials that emit as a result of incident radiation of other wavelengths, including those in the visible spectrum, by selecting the filter 10 appropriately to limit emission of incident visible light outside of that required to cause the material 23 to emit visible light. There are many luminescent materials that are excited by visible light and emit a substantially different wavelength visible light, including FITC that absorbs blue and emits green, and Texas Red that absorbs green and emits red. Luminescent materials that absorb non-visible light and emit visible light are preferred as the incident light does not detract from the visibility of the emitted visible light.

The bulb 9 can be pulsed at any frequency that tends to enhance the visibility of the emitted radiation. If the frequency is too low, the user may not notice the pulsing of the emitted radiation, particularly when the user is moving back and forth attempting to find it. If the frequency is too great then the pulse may tend to appear continuous, particularly if the bulb 9 does not extinguish quickly. A frequency of between 0.5 and 3 hertz is preferred for most users, although the principles described herein are not limited to that range.

In the preferred embodiment, the bulb 9 was pulsed on for 0.5 seconds and left off for 0.5 seconds for a pulse frequency of 1 hertz and a pulse duration of 0.5 seconds.

As mentioned previously, when phosphorescent materials are used the emitted radiation from the material should cease sufficiently prior to the next pulse of the lamp 1 in order to distinguish one pulse from the next.

Additional benefits of the system 6 include reduced power consumption due to the use of pulsed rather than continuous power. It is possible to run the system 6 from a battery source 15 for reasonable working periods prior to recharging the battery source 15. Consequent modifications to the control unit 5 to run from low voltage DC power would be evident to a person skilled in the art.

In addition, when the bulb 9 is not running continuously the lamp 1 is cooler to the touch. This makes it safer to use. As well and as mentioned previously, it is advantageous to increase the amount of ultraviolet incident exciting or stimulating radiation generated by the bulb 9 by increasing the voltage at which the bulb 9 is driven. Increasing the voltage by 25% over nominal rating (for example, a driving a nominal 100 volt bulb at 125 volts has been found to leave sufficient bulb life, while significantly increasing the intensity of ultraviolet exciting or stimulating radiation as compared to the increase in other wavelength incident radiation. This is due to the increased temperature at which the bulb 9 operates internally. The increased temperature can greatly reduce the life of the bulb 9; however, with pulsed use the bulb 9 is not activated for long periods and the reduction in life is less noticeable.

Figure 3:
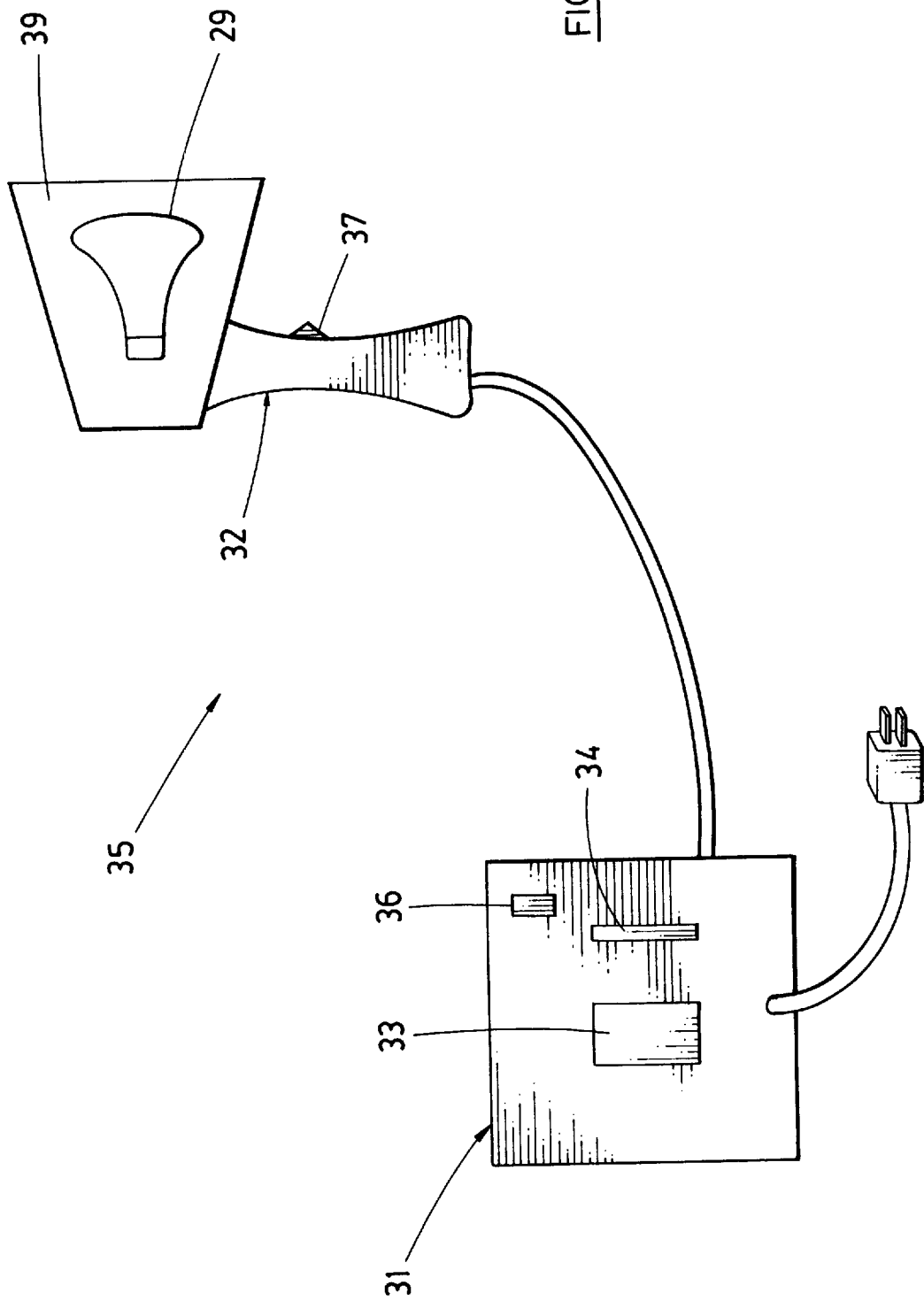
FIG. 3 is a diagrammatic side elevation view of a mercury vapour lamp system according to a preferred embodiment of the present invention.

Referring to FIG. 3, a further preferred embodiment uses a discharge bulb 29, such as a mercury vapour bulb 29, and a control unit 31 separated from lamp 32. The control unit 31 and the lamp 32 are separated because the control unit 31 uses a substantial mechanical ballast 33 that would make the lamp 32 too heavy for handheld use. The control unit 31 incorporates a strobing circuit 34. The control unit 31 and lamp 32 are a lamp system 35. The bulb 29 does not have a fluorescent coating that might otherwise be used where it is desirable to convert ultraviolet light from the bulb 9 to visible light.

The operation of the system 35 is similar to that of the system 6. The system 35 is turned on at a control switch 36. A momentary lamp switch 37 is depressed and the lamp 32 is aimed at an object to be tested. The strobing circuit 34 pulses the bulb 29 on and off, while a filter 39 limits visible light in a manner similar to the filter 10. Luminescent material on the object, if any, emits radiation that pulses on and off.

Although the mercury vapour lamp system 35 is generally more expensive to implement than the halogen lamp system 6, the system 35 tends to have a higher intensity of ultraviolet light.

It is possible to incorporate the control unit 31 into the lamp 32 so that the entire system 35 would be handheld and operate in a manner similar to the system 6; however, this requires an electronic ballast which is relatively expensive.

It is also possible to use a discharge bulb 29 that is excited with RF electronic energy and does not require a ballast 33. This simplifies the control unit 31 and reduces expense in manufacturing.

Figure 4:
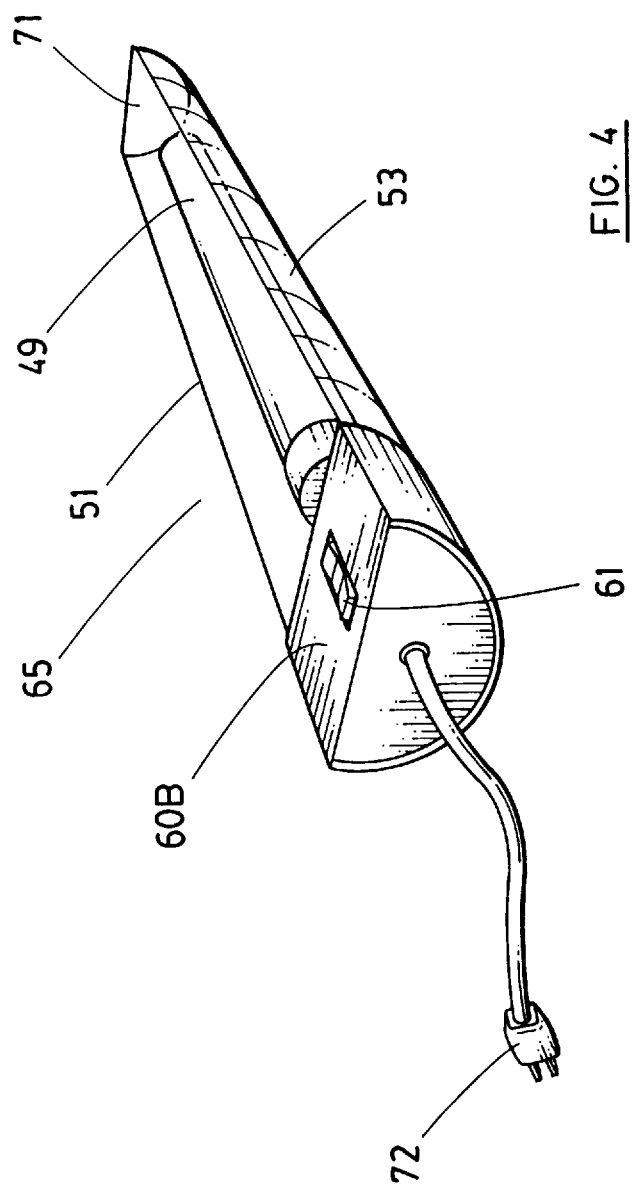
FIG. 4 is a perspective view of a fluorescent lamp system according to a preferred embodiment of the present invention.
Figure 5:
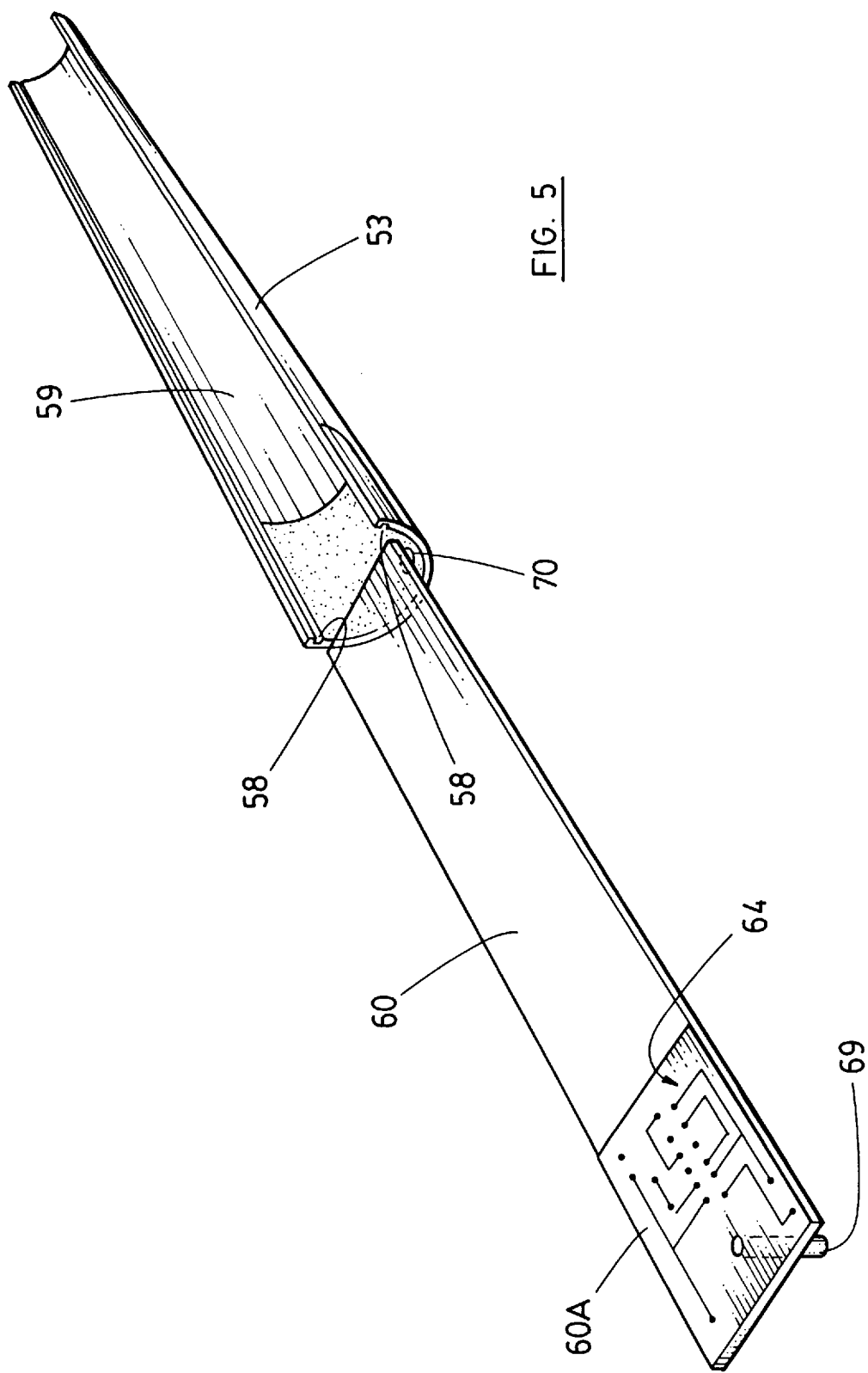
FIG. 5 is an exploded perspective view of certain components of the fluorescent lamp system of FIG. 4.

Referring to FIG. 4, a further embodiment uses a fluorescent bulb 49 in a fluorescent lamp 51. The lamp 51 has a wand shape and is particularly useful in tight spaces. As shown in FIG. 5, a back casing 53 has a U-shaped cross-section with opposing slots 58 along either side of the U. The back casing 53 is opaque and the a substantial portion of the interior is coated with a reflective material 59. The slots 58 hold a transmissive shield 60 over the fluorescent bulb 49. One end of the shield 60 forms a printed circuit board 60A. The reflective material 59 need not extend across the casing under the board 60A.

The portion of the casing 53 surrounding the board 60A is enclosed by a housing 60B. The housing 60B holds a three way toggle switch 61 for ON STEADY-OFF-ON STROBING. The board 60A holds a DC inverter and a strobing circuit. The DC inverter converts from DC to AC power for use by the fluorescent bulb 49, while the strobing circuit pulses that power on and off to the fluorescent bulb 49. The components of the board 60A form a control unit 64. The lamp 51 and control unit 64 form an integral fluorescent lamp system 65.

A simple method for fixing the board 60A, casing 53 and housing 60B is to create them from injection moulded plastic with a boss 69 extending from the circuit board 60A above a hole 70 in the casing 53. A corresponding hole, not shown, appears in the housing 60B, the housing is placed over the casing and a screw, not shown extends through the respective holes in the housing 60B and the casing 53 into the boss 69. A cap 71 encloses the end of the casing opposite the housing 60B. The back casing 53 should extend beyond the shield 60 in order to distance the shield 60 from debris that may be on a bench or other work area where the lamp system 65 is placed.

A plug 72 is provided for connection to a DC source, for example a waist mounted DC battery pack, not shown.

The bulb 49 may be either a black light (BL) or a blacklight blue (BLB) fluorescent bulb 49 selected to emit increased amounts of ultraviolet radiation if the system 65 is to be used in conjunction with a luminescent material that emits under ultraviolet incident light. As a BLB bulb 49 is selected to emit primarily non-visible wavelengths of an ultraviolet frequency, the shield 60 may be clear or even made from a wire mesh or protective material, as long as it is ultraviolet transmissive. In this case the shield 60 is provided primarily to protect the bulb 49 from damage and to keep the bulb 49 clean. If the bulb 49 is a BL bulb 49 then the shield 60 will also need to filter light in a manner similar to that of the filters 10, 39. Other fluorescent bulbs 49 having differing spectrums may be used where they have sufficient intensity in a given wavelength that is required for incident light.

In operation, the lamp 51 is put into a strobing mode by switching to ON STROBING at the switch 61. The DC inverter converts power from the plug 72 to alternating current, while the strobing circuit pulses that power to the bulb 49. The lamp 51 is shone near to a body, and luminescent material on the body, if any, is illuminated and emits visible radiation that pulses on and off.

The system 65 is designed to be a low cost, low power consumption alternative to the systems 6, 35. In most cases it will be desirable to simply operate from a fixed voltage DC source. However, the lamp system 65 can be used with AC power by replacing the DC inverter with an AC ballast. Alternatively, the system could be provided with a DC inverter/AC ballast connected to a voltage switch for selected frequencies and voltage, for example DC 12 volts and AC 120 V 60 Hz, or for automatic sensing. The plug 72 could be adapted for various outlets or terminals.

Fluorescent bulbs 49 have a relatively low intensity. The pulsing on and off of the emitted radiation is particularly useful to enhance what is otherwise a relatively low intensity of emitted radiation. It is also useful to overdrive the bulb 49 as described for the lamp system 6 for the generation of higher intensity emitted radiation.

Each lamp system 6, 35 or 65 can be sold as a kit along with the luminescent material that matches the particular radiation incident from the system 6, 35 or 65. Alternatively, each lamp system 6, 35 or 65 may be sold separate from corresponding luminescent material for later combination into a kit and use by a user.

As is evident from the different embodiments described above, the principles of the invention are not limited to any one bulb type or control system configuration. For example, a laser light source could be used with appropriate luminescent materials to provide a high intensity of specific wavelength incident radiation.

It will be understood by those skilled in the art that this description is made with reference to the preferred embodiments and that it is possible to make other embodiments employing the principles of the invention which fall within its spirit and scope as defined by the following claims.

We claim:

1. A hand held lamp system for locating faults using luminescent material that absorbs ultraviolet electromagnetic radiation of a first wavelength, converts that energy and emits a second visible wavelength light, the system comprising:

a lamp for generating incident ultraviolet electromagnetic radiation of the first wavelength;

a bulb in the lamp, the bulb generating ultraviolet electromagnetic radiation, including radiation of the first wavelength and other wavelengths, and generating visible light; and a control unit for repeatedly pulsing the bulb on and off at a pulse repetition frequency of substantially 0.5 Hz to less than 3 Hz, and with a bulb on duration which is long enough for the material to begin emitting the second wavelength, and with a bulb off duration which is long enough for the material to substantially stop emitting the second wavelength, the pulse repetition frequency, the bulb on duration and the bulb off duration all timed for the human eye to recognize the pulse of second wavelength light.

2. The lamp system of claim 1, wherein the lamp further comprises a filter for allowing electromagnetic radiation of the first wavelength to be emitted from the lamp while the filter limits visible light outside of the first wavelength from emitting from the lamp.

3. The lamp system of claim 1, wherein the first wavelength is approximately 360 nanometers.

4. The lamp system of claim 1, wherein the control unit pulses the bulb at a frequency between 0.5 and 3 Hz.

5. The lamp system of claim 1, wherein the lamp further comprises a handle for an operator to hold and aim the lamp, and a switch adjacent the handle for one handed operation of the lamp.

6. The lamp system according to claim 1, wherein the bulb comprises a halogen bulb.

7. The lamp system according to claim 1, wherein the bulb comprises a mercury vapour bulb, and wherein the control unit comprises (i) a strobing circuit for pulsing the bulb on and off, and (ii) a ballast.

8. The lamp system according to claim 1, wherein the bulb comprises an elongated fluorescent tube, and the lamp further comprises an elongated back casing for receiving the tube, the back casing being open on one side and coated internally with a reflective material.

9. The lamp system according to claim 8, wherein a shield encloses the back casing over the tube, and the shield is transmissive of the first wavelength radiation.

10. The lamp system according to claim 9, wherein the back casing and the shield extend into a housing for the control unit which is at least partially formed on a printed circuit hoard extending from the shield into the housing.

11. The lamp system according to claim 10, wherein the casing has a U-shaped profile and has opposing slots into which the shield is placed.

12. The lamp system of claim 10, wherein there is a duration between the bulb pulsing off and the bulb pulsing on, and the duration is greater than the time it takes for the material to cease emitting radiation after the bulb is pulsed off, to cause material on which the lamp is shone to emit radiation of the second wavelength pulsing on and off.

13. The lamp system of claim 12, wherein the material is phosphorescent.

14. The lamp system of claim 1, wherein the material is fluorescent.

15. A kit, comprising:
a hand held lamp system including:
a lamp for generating incident ultraviolet electromagnetic radiation of a first wavelength, and
a bulb in the lamp, the bulb generating ultraviolet electromagnetic radiation, including radiation of the first wavelength and other wavelengths, and generating visible light;
a control unit for repeatedly pulsing the bulb on and off at a pulse repetition frequency of substantially 0.5 Hz to less than 3 Hz, and with a bulb on duration which is long enough for the material to begin emitting the second wavelength, and with a bulb off duration which is long enough for the material to substantially stop emitting the second wavelength, the pulse repetition frequency, the bulb on duration and the bulb off duration all timed for the human eye to recognize the pulse of second wavelength light; and
a luminescent material that absorbs electromagnetic radiation of the first wavelength, converts that energy, and emits a second visible wavelength light to cause material on which the lamp is shone to emit radiation of the second wavelength pulsing on and off.

16. A method of locating luminescent material that absorbs electromagnetic energy of an ultraviolet electromagnetic radiation of a first wavelength, converts that energy and emits electromagnetic radiation of a substantially different visible second wavelength, the method comprising the steps of:
generating ultraviolet electromagnetic radiation, including radiation of the first wavelength and other wavelengths, and generating visible light from a bulb, and repeatedly pulsing the bulb on and off at a pulse repetition frequency of substantially 0.5 Hz to less than 3 Hz, and with a bulb on duration which is long enough for the material to begin emitting the second wavelength, and with a bulb off duration which is long enough for the material to substantially stop emitting the second wavelength, the pulse repetition frequency, the bulb on duration and the bulb off duration being timed for the human eye to recognize the pulse of second wavelength light;
while pulsing the bulb on, increasing the amount of ultraviolet electromagnetic radiation of the first wavelength emitting from the bulb relative to the amount of visible light emitting from the bulb by powering the bulb at a higher than nominal rating for the bulb to increase the temperature of the bulb over that which would result if the bulb was run at a nominal rating voltage for the bulb, and illuminating the material with the ultraviolet radiation of the first wavelength emitting from the bulb, to cause the material to fluoresce and pulse upon illumination.

17. The method of claim 16, wherein the ultraviolet electromagnetic radiation and visible light generated from the bulb are passed through a filter that allows the ultraviolet electromagnetic radiation of the first wavelength to pass and otherwise limits the amount of visible light passing through the filter.

18. A hand held lamp system for locating faults using luminescent material that absorbs ultraviolet electromagnetic radiation of a first wavelength, converts that energy and emits a second visible wavelength light, the system comprising:
a lamp for generating incident ultraviolet electromagnetic radiation of the first wavelength;
a bulb in the lamp, the bulb generating ultraviolet electromagnetic radiation, including radiation of the first wavelength and other wavelengths, and generating visible light; and
a control unit for, in normal operation, repeatedly pulsing the bulb on and off, the control unit increasing the amount of ultraviolet electromagnetic radiation of the first wavelength emitting from the bulb relative to the amount of visible light emitting from the bulb by repeatedly powering the bulb at a higher electrical rating than the nominal electrical rating for the bulb to increase the temperature of the bulb over that which would result if the bulb was run at the nominal rating for the bulb, to cause material on which the lamp is shone to emit radiation of the second wavelength pulsing on and off, the control unit pulsing the bulb with a bulb-on duration, a bulb-off duration, and a pulse frequency which are all timed to cause each pulse repetition of the second wavelength to be visible to the unaided human eye.

19. A lamp system according to claim 18, wherein said bulb comprises a tungsten filament bulb.

20. A system according to claim 18, wherein the electrical rating comprises a voltage.

21. A kit, comprising:
a hand held lamp system including:
a lamp for generating incident ultraviolet electromagnetic radiation of a first wavelength, and
a bulb in the lamp, the bulb generating ultraviolet electromagnetic radiation, including radiation of the first wavelength and other wavelengths, and generating visible light;
a control unit for, in normal operation, repeatedly pulsing the bulb on and off, the control unit increasing the amount of ultraviolet electromagnetic radiation of the first wavelength emitting from the bulb relative to the amount of visible light emitting from the bulb by repeatedly powering the bulb at an electrical rating which is higher than the nominal electric rating for the bulb to increase the temperature of the bulb over that which would result if the bulb was powered at the nominal electrical rating for the bulb, the control unit pulsing the bulb with a bulb-on duration, a bulb-off duration, and a pulse frequency which are all timed to cause each pulse repetition of the second wavelength to be visible to the unaided human eye; and a luminescent material that absorbs electromagnetic radiation of the first wavelength, converts that energy, and emits a second visible wavelength light to cause material on which the lamp is shone to emit radiation of the second wavelength pulsing on and off.

22. A kit according to claim 21, wherein said bulb comprises a tungsten filament bulb.

23. A kit according to claim 21, wherein the electrical rating comprises a voltage.

24. A method of locating luminescent material that absorbs electromagnetic energy of an ultraviolet electromagnetic radiation of a first wavelength, converts that energy and emits electromagnetic radiation of a substantially different visible second wavelength, the method comprising the steps of:

generating ultraviolet electromagnetic radiation, including radiation of the first wavelength and other wavelengths, and generating visible light from a bulb, and, in normal operation, repeatedly pulsing the bulb on and off;

while pulsing the bulb on, increasing the amount of ultraviolet electromagnetic radiation of the first wavelength emitting from the bulb relative to the amount of visible light emitting from the bulb by powering the bulb at an electrical rating which is higher than the nominal electric rating for the bulb to increase the temperature of the bulb over that which would result if the bulb was run at a nominal electrical rating for the bulb, and illuminating the material with the ultraviolet radiation of the first wavelength emitting from the bulb, to cause the material to fluoresce and pulse upon illumination, the control unit pulsing the bulb with a bulb-on duration, a bulb-off duration, and a pulse frequency which are all timed to cause each pulse repetition of the second wavelength to be visible to the unaided human eye.

25. A method according to claim 24, wherein said step of generating ultraviolet radiation includes the step of generating the radiation of the first wavelength and other wavelengths and the visible light with a tungsten filament bulb.

26. A method according to claim 24, wherein the electrical rating comprises a voltage.

27. A hand held lamp system for locating faults using luminescent material that absorbs ultraviolet electromagnetic radiation of a first wavelength, converts that energy and emits a second visible wavelength light, the system comprising:

hand-held means for an operator to grip said lamp system;

a lamp for generating incident ultraviolet electromagnetic radiation of the first wavelength;

a tungsten filament bulb in the lamp, the tungsten filament bulb generating ultraviolet electromagnetic radiation, including radiation of the first wavelength and other wavelengths, and generating visible light; and a control unit for, in normal operation, repeatedly pulsing the tungsten filament bulb on and off to cause (i) the luminescent material to convert the absorbed ultraviolet radiation to pulses of the second wavelength light, and (ii) the converted pulses of second wavelength light to be recognizable by a human eye as pulses, the control unit pulsing the bulb with a bulb-on duration, a bulb-off duration, and a pulse frequency which are all timed to cause each pulse repetition of the second wavelength to be visible to the unaided human eye.

* * * * *